United States Patent

Quash et al.

Patent Number: 6,117,902
Date of Patent: Sep. 12, 2000

[54] 6,8-DIMERCAPTOOCTANOIC ACID DERIVATIVES SUBSTITUTED AT THE 6-S AND/OR 8-S POSITION WITH THE (3-METHYLTHIOPROPANOYL) RADICAL AND PHARMACEUTICAL COMPOSITIONS INTENDED FOR THE TREATMENT OF CANCEROUS TUMORS

[75] Inventors: Gérard Anthony Quash, Francheville; Jacques Gore, Calluire et Cuire; Guy Fournet, Villeurbanne, all of France

[73] Assignee: Galderman Research & Development, S.N.C. Sophia Abtipolis, Cedex, France

[21] Appl. No.: 09/281,654

[22] Filed: Mar. 30, 1999

[30] Foreign Application Priority Data

Apr. 1, 1998 [FR] France .................................. 98-04041

[51] Int. Cl.⁷ ...................... A61K 31/225; A61K 31/495; C07C 327/04; C07C 327/18; C07D 295/185
[52] U.S. Cl. .......................... 514/513; 514/255; 544/358; 544/386; 558/251; 558/255
[58] Field of Search .................................. 558/251, 255; 544/358, 386; 514/513, 255

[56] References Cited

FOREIGN PATENT DOCUMENTS

WO 96/20701  7/1996  WIPO .

OTHER PUBLICATIONS

Quash, G et al "Methional derived from 4–methylthio–2–oxobutanoate is a cellular mediator of apoptosis in BAF3 lymphoid cells" Biochem. J. vol. 305 pp. 1017–1025, 1995.

*Primary Examiner*—Gary Geist
*Assistant Examiner*—Leigh C. Maier
*Attorney, Agent, or Firm*—BakerBotts LLP

[57] ABSTRACT

The present invention provides 6,8-Dimercaptooctanoic acid derivatives substituted at the 6-S and/or 8-S position with the (3-methylthiopropanoyl) radical, wherein they correspond to the following formula (I):

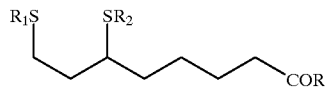

in which:

R represents $OR_3$ or

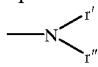

$R_3$ representing a hydrogen atom, a linear or branched alkyl radical, or a radical of the formula

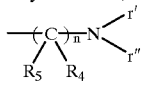

n being an integer from 1 to 10 and r' and r", which are identical or different, representing a hydrogen atom, a linear or branched alkyl radical or, taken together, form with the nitrogen atom, a nitrogen-containing heterocycle optionally substituted with an optionally substituted oxygen or nitrogen atom,

$R_5$ and $R_4$, identical or different, represent a hydrogen atom or a linear or branched alkyl radical, $R_1$ and $R_2$, which are identical or different, represent a hydrogen atom, a radical —$COCH_3$ or a radical of formula:

$$-CO(CH_2)_2SCH_3 \qquad (II)$$

with the proviso that at least one of the radicals $R_1$ or $R_2$ represents a radical of formula (II) and the R and S enantiomers and their racemate as well as the salts of the said compounds of formula (I). The present invention also provides pharmaceutical compositions, and method of treatment and prevention of cancerous tumours.

17 Claims, 8 Drawing Sheets

FIGURE 1

- MTOB represents 4-methylthio-2-oxobutanoic acid
- MTPA represents methylthiopropionic acid
- $E_1$ represents the decarboxylase of the dehydrogenase-branched chain oxo acid complex whose cofactor is thiamine pyrophosphate,
- $E_2$ represents the transacylase of the dehydrogenase-branched chain oxo acid complex whose cofactor is thioctic acid,
- ALDR represents aldehyde reductase,
- ALDH represents aldehyde dehydrogenase,
- CoASH represents acetyl coenzyme A,
- NADH/NAD represents nicotinamide adenin dinucleotide, and
- NADPH/NADP represents nicotinamide adenine dinucleotide phosphate.

FIGURE 13

6,8-DIMERCAPTOOCTANOIC ACID DERIVATIVES SUBSTITUTED AT THE 6-S AND/OR 8-S POSITION WITH THE (3-METHYLTHIOPROPANOYL) RADICAL AND PHARMACEUTICAL COMPOSITIONS INTENDED FOR THE TREATMENT OF CANCEROUS TUMORS

FIELD OF THE INVENTION

The present invention relates to 6,8-dimercaptooctanoic acid derivatives substituted at the 6-S and/or 8-S position with the (3-methylthiopropanoyl) radical and their use as cell apoptosis inducing agents.

The present invention also relates to a pharmaceutical composition containing, as active agent, at least one 6,8-dimercaptooctanoic acid derivative substituted at the 6-S and/or 8-S position with the (3-methylthiopropanoyl) radical, in a pharmaceutically acceptable excipient, especially for the treatment, regression and prevention of cancerous tumours.

BACKGROUND OF THE INVENTION

One type of the mechanisms of cell death is so called as "Apoptosis", and has been described, inter alia, by KERR J. F. R. et al., J. Cancer, 265, 239 (1972). It is understood that apoptosis is a highly selective form of cellular suicide which is characterized by easily observable morphological and biochemical phenomena. Condensation of chromatin associated or not with exonucleases activation, formation of apoptotic bodies and fragmentation of deoxyribonucleic acid (DNA) to 180–200 base pairs DNA fragments thereby providing an easily recognizable profile by agarose gel electrophoresis are thus observed.

A wide variety of natural or synthetic anticancer drugs is currently available.

Alkylating agents such as cyclophosphamides, nitrosoureas such as 1,3-bis (2-chloroethyl)-1-nitrosourea (BCNU), intercalating agents such as actinomycin D or adriamycin, purine or pyrimidine base analogues such as 6-thioguanine and 5-fluorouracil, inhibitors of de novo synthesis of purine bases such as methotrexate and tubulin polymerization inhibitors such as Taxol® may be cited inter alia as antineoplastic drugs.

One of the main disadvantages of the use of these substances is the lack of a selective apoptotic activity against tumour cells. Thus, the major problem for preparing such compounds is to design and prepare molecules which induce maximum apoptosis in tumour tissues while injuring healthy tissues as little as possible and in a reversible manner.

Figure 1:
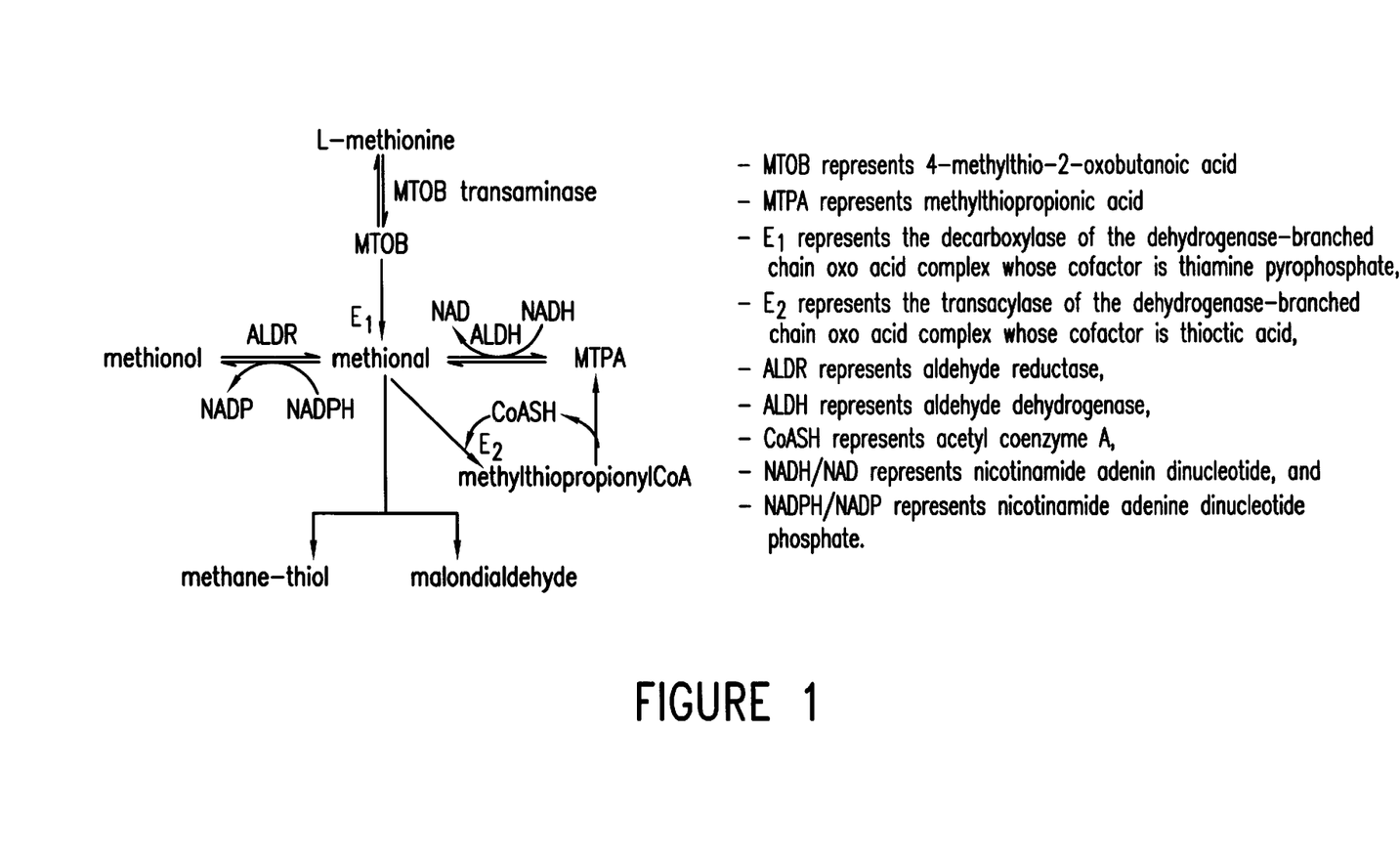
FIG. 1 represents the metabolic pathway for methional.

In order to overcome the lack of selectivity, the applicant has already proposed, particularly in Patent Application WO 96/20701, the use apoptosis-inducing compounds chosen from methional, malonaldehyde and any factor capable to promote an increase of the intracellular level of these compounds, or interfere with the metabolism of methional which is displayed in FIG. 1 (QUASH et al., Biochem. J. 305, 1017 (1995)).

Ester compounds of L-methionine and pyridoxal have been described in Patent Application WO 96/20701 as factors capable of increasing the intracellular level of methional. In effect, these compounds inhibit the conversion of 4-methylthio-2-oxobutanoic acid (MTOB) to methionine by the MTOB transaminase enzyme, thereby causing accumulation of MTOB which is a direct precursor of methional (See FIG. 1) (ROCH et al., Biochem. J. 313, 973 (1996)).

However, the selectivity of methional and malonaldehyde against tumour cells was again proved insufficient since these compounds inhibit the growth of both tumour cells and normal cells to the same extent.

The use of an aminothioester derivative, designated AMPALTE, as an inhibitor of the enzyme aldehyde dehydrogenase (ALDH), i.e., an enzyme involved in the conversion of methional to methylthiopropionic acid, thereby promoting accumulation of methional, has also been described by the applicant in Patent Application FR-9704283. This compound is a selective inhibitor of the growth of transformed cells which are resistant to apoptosis because of the overexpression of the anti-apoptotic gene $bcl_2$.

Such a compound is therefore more specifically intended for pathological conditions characterized by overexpression of the $bcl_2$ gene such as breast cancers, B-cell lymphomas, leukaemias, neuroblastomas, prostate adenocarcinomas, prolactinomas and other pituitary adenomas.

It was therefore desirable to develop a therapeutic strategy which is selective against tumour cells and to target a large number of cancer pathologies.

Following numerous studies on various methional derivatives, it has been observed that the derivatives comprising methional coupled by a thioester bond to thioctic acid had a highly selective apoptotic activity against transformed and tumour cells, as demonstrated by the experimental data presented in the application.

Such an activity makes the compounds of the invention useful in antitumour therapeutic treatment.

SUMMARY OF THE INVENTION

The present invention thus provides as novel active compounds, 6,8-dimercaptooctanoic acid derivatives substituted at the 6-S and/or 8-S position with the (3-methylthiopropanoyl) radical and the use thereof as agents inducing apoptosis of transformed and tumour cells.

The present invention also provides pharmaceutical compositions containing an effective amount of at least an active compound according to the present invention in a pharmaceutically acceptable excipient.

The present invention further provides pharmaceutical compositions for the treatment, regression, and prevention of cancer containing as antitumour therapeutic agent, an effective amount of at least an active compound according to the present invention.

The present invention firther provides a method of inducing apoptosis in transformed and tumour cells which comprises administering to a subject an effective amount of at least an active compound according to the present invention.

Finally, the present invention provides a method for the treatment, regression, and prevention of cancer in a subject which comprises administering to a subject an effective amount of at least an active compound according to the present invention.

DETAILED DESCRIPTION OF THE INVENTION

In accordance with the invention, the compounds may be represented by the following formula (I):

(I)

in which:

R represents $OR_3$ or $R_3$ representing a hydrogen atom, a linear or branched alkyl radical, or a radical of the formula n being an integer from 1 to 10 and r' and r", which are identical or different, representing a hydrogen atom, a linear or branched alkyl radical, or taken together, form with the nitrogen atom, a nitrogen-containing heterocycle optionally substituted with an optionally substituted oxygen or nitrogen atom, $R_5$ and $R_4$, identical or different, represent a hydrogen atom, a linear or branched alkyl radical, $R_1$ and $R_2$, which are identical or different, represent a hydrogen atom, a radical —$COCH_3$, or a radical of formula:

$$—CO(CH_2)_2SCH_3 \qquad (II)$$

with the proviso that at least one radical $R_1$ or $R_2$ represents a radical of formula (II) and the R and S enantiomers and their racemate as well as the salts of the said compounds of formula (I).

Among the linear or branched alkyl radicals, a radical having from 1 to 12 carbon atoms, and more particularly from 1 to 6 carbon atoms, is preferred according to the invention. Among them, there may be mentioned the methyl, ethyl, isopropyl, n-butyl isobutyl and tert-butyl radicals.

According to the invention index "n" is generally between 2 to 6, the divalent radical being preferably ethylene, propylene, butylene or methyl-2 propane-1,2 diyl.

When radicals r' and r" form a nitrogen-containing heterocycle, the latter may be morpholine, pyrrolidine, piperazine, homopiperazine and a N-alkyl ($C_1$–$C_6$) piperazine.

The carbon atom at the $C_6$ position being asymmetric, the compounds of the invention may therefore exist either in the form of R and S enantiomers or in racemic form.

When the compounds of the invention according to Formula (I) are in the form of salts, they are either salts from a mineral or organic base when the compounds have a carboxylic acid function or salts from a mineral or organic acid when the compounds have salifying amino function.

Salts of a base, may be for example radium, potassium and calcium salts, whereas salts of an acid may be halides, nitrates, sulfates, sulfonates, carboxylates, thiocyanates and phosphates.

In a preferred embodiment, the salts are ammonium halides namely iodides such as trimethylammonium iodides or N-alkyl piperazonium iodides.

Among the compounds of formula (I) which are monosubstituted at the 6 or 8 position or which are disubstituted, there may be mentioned in particular:

| No. | Compounds |
|---|---|
| 1- | methyl 6-mercapto-8-S-(3-methylthiopropanoyl)octanoate, (formula I: $R_1$ = —$CO(CH_2)_2$—$SCH_3$; $R_2$ = H; R = $OCH_3$); |
| 2- | methyl 6-S-(3-methylthiopropanoyl) 8-mercaptooctanoate, |

-continued

No. Compounds (formula I: $R_1$ = H; $R_2$ = —CO(CH$_2$)$_2$—SCH$_3$; R = OCH$_3$);
3- methyl 6-S,8-S-bis(3-methylthiopropanoyl)octanoate,
(formula I: $R_1$ = $R_2$ = —CO(CH$_2$)$_2$—SCH$_3$; R = OCH$_3$);
4- tert-butyl 6-mercapto-8-S-(3-methylthiopropanoyl)octanoate,
(formula I: $R_1$ = —CO(CH$_2$)$_2$—SCH$_3$; $R_2$ = H; R = O-tertC$_4$H$_9$);
5- tert-butyl 6-S-(3-methylthiopropanoyl) 8-mercaptooctanoate,
(formula I: $R_1$ = H; $R_2$ = —CO(CH$_2$)$_2$—SCH$_3$; R = O-tertC$_4$H$_9$);
6- tert-butyl 6-S,8-S-bis(3-methylthiopropanoyl)octanoate,
(formula I: $R_1$ = $R_2$ = —CO(CH$_2$)$_2$—SCH$_3$; R = O-tertC$_4$H$_9$);
7- n-butyl 6-mercapto-8-S-(3-methylthiopropanoyl)octanoate,
(formula I: $R_1$ = —CO(CH$_2$)$_2$—SCH$_3$; $R_2$ = H; R = O-nC$_4$H$_9$);
8- n-butyl 6-S-(3-methylthiopropanoyl) 8-mercaptooctanoate,
(formula I: $R_1$ = H; $R_2$ = —CO(CH$_2$)$_2$—SCH$_3$; R = O-nC$_4$H$_9$);
9- n-butyl 6-S,8-S-bis(3-methylthiopropanoyl)octanoate,
(formula I: $R_1$ = $R_2$ = —CO(CH$_2$)$_2$—SCH$_3$; R = O-nC$_4$H$_9$);
10- 6-mercapto-8-S-(3-methylthiopropanoyl)octanoic acid,
(formula I: $R_1$ = —CO(CH$_2$)$_2$—SCH$_3$; $R_2$ = H; R = OH);
11- 6-S-(3-methylthiopropanoyl)-8-mercaptooctanoic acid,
(formula I: $R_1$ = H; $R_2$ = —CO(CH$_2$)$_2$—SCH$_3$; R = OH);
12- 6-S,8-S-bis(3-methylthiopropanoyl)octanoic acid,
(formula I: $R_1$ = $R_2$ = —CO(CH$_2$)$_2$—SCH$_3$; R = OH);
13- ethyl 6-mercapto-8-S-(3-methylthiopropanoyl)octanoate,
(formula I: $R_1$ = —CO(CH$_2$)$_2$—SCH$_3$; $R_2$ = H; R = OC$_2$H$_5$)
14- ethyl 6-S-(3-methylthiopropanoyl) 8-mercaptooctanoate,
(formula I: $R_1$ = H; $R_2$ = —CO(CH$_2$)$_2$—SCH$_3$; R = OC$_2$H$_5$);
15- ethyl 6-S,8-S-bis(3-methylthiopropanoyl)octanoate,
(formula I: $R_1$ = $R_2$ = —CO(CH$_2$)$_2$—SCH$_3$; R = OC$_2$H$_5$);
16- isopropyl 6-mercapto-8-S-(3-methylthiopropanoyl)octanoate,
(formula I: $R_1$ = —CO(CH$_2$)$_2$—SCH$_3$; $R_2$ = H; R = OCH(CH$_3$)$_2$);
17- isopropyl 6-S-(3-methylthiopropanoyl)8-mercaptooctanoate,
(formula I: $R_1$ = H; $R_2$ = —CO(CH$_2$)$_2$—SCH$_3$; R = OCH(CH$_3$)$_2$);
18- isopropyl 6-S,8-S-bis(3-methylthiopropanoyl)octanoate,
(formula I: $R_1$ = $R_2$ = —CO(CH$_2$)$_2$—SCH$_3$; R = OCH(CH$_3$)$_2$);
19- (2'-trimethylammoniumethyl)6-mercapto-8-S-(3-methylthiopropanoyl) octanoate iodide,
(formula I: $R_1$ = —CO(CH$_2$)$_2$—SCH$_3$; $R_2$ = H; R = O(CH$_2$)$_2$N$^+$(CH$_3$)$_3$I$^-$);
20- (2'-trimethylammoniumethyl)6-S-(3-methylthiopropanoyl)8-mercaptooctanoate iodide,
(formula I: $R_1$ = H; $R_2$ = —CO(CH$_2$)$_2$—SCH$_3$; R = O(CH$_2$)$_2$N$^+$(CH$_3$)$_3$I$^-$);
21- (2'-trimethylammoniumethyl)6-S,8-S-bis(A-methylthiopropanoyl)octanoate iodide,
(formula I: $R_1$ = $R_2$ = —CO(CH$_2$)$_2$—SCH$_3$; R = O(CH$_2$)$_2$N$^+$(CH$_3$)$_3$I$^-$);
22- [6-S,8-S-bis(3-methylthiopropanoyl)octanoyl]-N-methylpiperazine, 23- methyl 6-S-acetyl, 8-S-(3-methylthiopropanoyl)octanoate,
(formula I: $R_1$ = —CO(CH$_2$)$_2$—SCH$_3$; $R_2$ = —COCH$_3$; R = —COH$_3$);
24- methyl 6-S-(3-methylthiopropanoyl), 8-S-acetyl octanoate,
(formula 1: $R_1$ = —COCH$_3$; $R_2$ = —CO(CH$_3$)$_2$—SCH$_3$; R = —OCH$_3$);
25- (2'-trimethyl ammoniumethyl) 6-S-acetyl, 8-S-(3-methylthiopropanoyl)octanoate iodide, and
(formula I: $R_1$ = —CO(CH$_2$)$_2$—SCH$_3$; $R_2$ = —COCH$_3$; R =—O(CH$_2$)$_2$N$^+$(CH$_3$)$_3$I$^-$);
26- (2'-trimethyl ammoniumethyl)6-S-(3-methylthiopropanoyl), 8-S-acetyl octanoate iodide,
(formula I: $R_1$ = —COCH$_3$; $R_2$ = —CO(CH$_2$)$_2$—SCH$_3$; R = —O(CH$_2$)$_2$N$^+$(CH$_3$)$_3$I$^-$).

The (R) and (S) enantiomers of the above compounds will be designated hereinafter according to the number attributed to each compound followed by (R) or (S), and the racemates will be designated according to the number followed by (RS).

Figure 2:
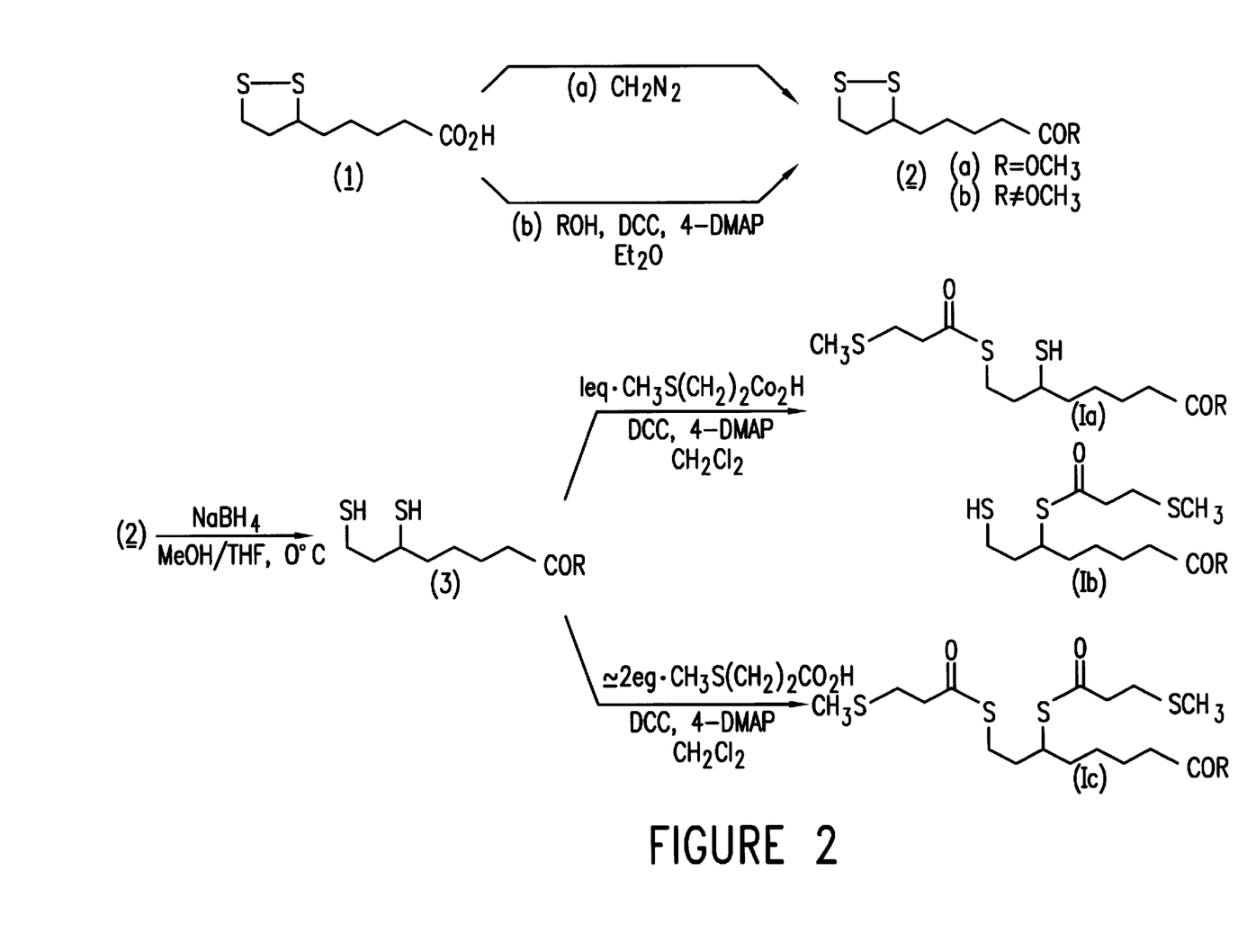
FIG. 2 represents the reaction scheme for obtaining the compounds of the formula (I).

The compounds of formula (I) according to the invention may be obtained according to the reaction scheme in FIG. 2.

The method of synthesis consists, in a first step, in esterifying the 6,8-thioctic acid or lipoic acid of formula (1) either in the presence of diazomethane when it is desired to obtain the ester of formula (2) in which R=OCH$_3$ or, for the other meanings, with an alcohol ROH in ether in the presence of dicyclohexylcarbodiimide (DCC) and 4-dimethylaminopyridine (4-DMAP). The esterification yield is generally about 80 to 99% relative to the starting acid.

The ester obtained (2) is then reduced in the presence of sodium borohydride in a methanol/tetrahydrofuran mixture to give the dithiol of formula (3) with a yield greater than about 95%.

Starting with the dithiol of formula (3), the compounds of formulae (Ia) and (Ib) are obtained by reacting 1 molar equivalent of 3-methylthiopropionic acid in dichloromethane in the presence of DCC and 4-DMAP. A mixture of (Ia) and (Ib) is thus obtained which can be separated by preparative chromatography on silica gel, but in which (Ia) is predominant (>90%). It is probable that the compounds (Ia) and (Ib) are interconvertible.

The compound of formula (Ic) is also obtained from the dithiol of formula (3) under the same conditions as above but by reacting a molar excess of 3-methylthiopropionic acid, preferably 3 molar equivalents. The reaction yield is about 60 to 80%.

If during the reaction, and despite the excess of 3-methylthiopropionic acid, one of the compounds of formulae (Ia) and/or (Ib) is formed, they can be separated by chromatography on silica gel.

The compounds of formula (I) (R=OH) can be obtained directly from lipoic acid by reduction and acylation with the aid of 3-methylthiopropionic acid.

The amides of formula (I) are easily accessible from thioctic acid by the same sequence, namely amidation, reduction and acylation.

The compounds of formula (I) wherein $R_1$ or $R_2$=—$OCH_3$ are directly obtained either from compound of Formula (Ia) or (Ib) by an acylation reaction using acetic anhydride in presence of pyridine.

Although reference has been made above to some specific conditions for the steps for the synthesis of the compounds according to the invention, it goes without saying that other variants of these conditions may be used, in particular as regards the esterification, amidation and acylation steps.

The invention also provides a pharmaceutical composition containing, an effective amount of at least one 6,8-dimercaptooctanoic acid derivative substituted at the 6-S and/or 8-S position with the (3-methylthiopropanoyl) radical of formula (I) as active agent, more particularly as agent inducing apoptosis of transformed and tumour cells, in a pharmaceutically acceptable excipient.

The pharmaceutical composition according to the present invention induces apoptosis, as defined above, selectively in transformed and cancerous cells.

More particularly, the present invention provides a pharmaceutical composition for the treatment, regression and prevention of cancerous tumours in a human or animal subject.

The pharmaceutical composition according to the invention comprises a physiologically acceptable medium and may be administered enterally, parenterally or topically.

Preferably, the pharmaceutical composition is packaged in a form suitable for application by the systemic route (for injection or infusion).

By the enteral route, the pharmaceutical composition may be provided in the form of tablets, gelatin capsules, sugar-coated tablets, syrups, suspensions, solutions, powders, granules, emulsions, or lipid or polymeric microspheres or nanospheres or vesicles allowing controlled release.

By the parenteral route, the composition may be provided in the form of solutions or suspensions for infusion or for injection.

By the topical route, the pharmaceutical composition according to the invention is more particularly intended for the treatment of the skin and the mucous membranes and may be provided in the form of salves, creams, milks, ointments, powders, impregnated pads, solutions, gels, sprays, lotions or suspensions.

It may also be provided in the form of lipid or polymeric microspheres or nanospheres or vesicles or of polymeric patches and of hydrogels allowing controlled release. When the composition is intended for use by the topical route, it may be provided either in anhydrous form or in aqueous form.

In the compositions according to the invention, the active compound of formula (I) is generally present in a concentration of between 0.1 and 10% by weight, preferably between 0.1 and 5% by weight, relative to the total weight of the composition.

The compositions as described above may of course contain other inert or even pharmacodynamically active additives or combinations of these additives, and in particular other antineoplastic agents, such as for example dexamethasone, cyclophosphamide, cisplatin, etoposide and BCNU (N,N-bis(2-chloroethyl)-N-nitrosourea), which are also capable of inducing apoptosis.

The active compounds of formula (I) according to the invention are generally administered at a daily dose of about 50 mg/kg to 100 mg/kg of body weight in 1 to 2 doses, the duration of the treatment being dependent on the pathological condition of the subjects.

The various aspects of the invention will appear more clearly on reading the various examples which follow which are intended to illustrate it.

EXAMPLES

Example 1

Preparation of methyl 6-mercapto-8-S-(3-methylthiopropanoyl)octanoate (compound No.1)

(a) Methyl 6, 8-dimercaptooctanoate

The starting methyl lipoate is a known compound which has been described by Gunsalus et al., J. Am. Chem. Soc. 1956, 78, 1763–1766.

85 mg of (2.25 mmol) of sodium borohydride are added at 0° C. in two portions to 444 mg (2.02 mmol) of methyl lipoate in solution in 25 ml of a methanol/tetrahydrofuran mixture (5/1).

After stirring for 40 min at 0° C., 5 N hydrochloric acid is dropwise poured until a stable white cloudiness appears. After evaporation of the solvent, the residue is taken up in ether and the organic phase is washed with a saturated aqueous sodium bicarbonate solution and then with a saturated sodium chloride solution. After drying over sodium sulphate and evaporation of the ether, 445 mg (99%) of the expected dithiol are obtained.

(b) Methyl 6-mercapto-8-S-(3-methylthiopropanoyl) octanoate 8 mg (0.065 mmol) of 4-dimethylaminopyridine are added to 192 mg (1.6 mmol) of 3-methylthiopropanoic acid in 0.6 ml of dichloromethane and then a solution of 355 mg (1.6 mmol) of methyl 6,8-dimercaptooctanoate as obtained above, in 1 ml of dichloromethane is introduced. 33 mg (1.6 mmol) of dicyclohexylcarbodiimide are then added at 0° C. and left for 5 min at 0° C. The mixture is then heated at 18° C. with stirring for 3 hours. After filtration and dilution of the filtrate in ether, the organic phase is washed with a saturated aqueous sodium chloride solution, dried over magnesium sulphate and the ether evaporated off. The residue obtained is then purified by chromatography on silica gel (25 g, eluent: petroleum ether/ethyl acetate 85/15) and 311 mg (60%) of the expected mercaptoester are isolated in the form of an almost colourless oil (contaminant 5 to 10% of methyl 6-S-(3-methylthiopropanoyl) 8-mercaptooctanoate).

Example 2

Preparation of methyl 6-S,8-S-bis(3-methylthiopropanoyl) octanoate (compound No.3)

This compound is obtained according to the same procedure as that described in Example 1(b) but using 3 molar equivalents of 3-methylthiopropionic acid.

The expected product is obtained with a yield of 75% in the form of an almost colourless oil.
$[\alpha]_D = -6.1$ (c: 1.93 CHCl$_3$) R series
$[\alpha]_D = +6.8$ (c: 2 CHCl$_3$) S series

Example 3
Preparation of isopropyl 6-mercapto-8-S-(3-methylthiopropanoyl)octanoate (compound No.16)

(a) Isopropyl lipoate 12 ml of anhydrous ether are added to 1 g (4.85 mmol) of lipoic acid, 1.1 g (5.33 mmol) of dicyclohexylcarbodiimide and 0.061 g (0.5 mmol) of 4-dimethylaminopyridine placed under nitrogen. After stirring for 10 min at room temperature, 0.41 ml (5.35 mmol) of isopropanol is added and the mixture is stirred for 15 hours.

After filtration of the solids and dilution of the filtrate in ether, the organic phase is washed with a 5% acetic acid solution in water and then with a saturated aqueous sodium bicarbonate solution and finally with a saturated aqueous sodium chloride solution.

After drying over sodium sulphate and evaporation of the solvent, the residue is filtered on silica gel (20 g, eluent: petroleum ether/ethyl acetate 85/15).

After evaporation of the elution solvent, 1.095 g (91%) of isopropyl lipoate are obtained in the form of a yellow oil.

(b) Isopropyl 6,8-dimercaptooctanoate

This compound is obtained according to the same procedure as that described in Example 1(a) by reduction of isopropyl lipoate with sodium borohydride.

Scale: 2 mmol, yield: 99% (almost colourless oil).

(c) Isopropyl 6-mercapto-8-S-(3-methylthiopropanoyl)octanoate

This compound is obtained according to the same procedure as that described in Example 1(b) by acylation of isopropyl 6,8-dimercaptooctanoate with the aid of one molar equivalent of 3-methylthiopropanoic acid. After purification by chromatography on silica gel, isopropyl 6-mercapto-8-S-(3-methylthiopropanoyl)octanoate is isolated in the form of an oil (yield: 60%) (contaminant: 5 to 10% of isopropyl 6-S-(3-methylthiopropanoyl) 8-mercaptooctanoate) and isopropyl 6-S,8-S-bis(3-methylthiopropanoyl) octanoate. Scale: 2 mmol, yield: 11%.

Example 4
Preparation of n-butyl 6-S,8-S-bis(3-methylthiopropanoyl)octanoate (compound No.9)

(a) n-Butyl lipoate

According to the same procedure as that described in Example 3(a) for the synthesis of isopropyl lipoate, the esterification of lipoic acid with the aid of n-butanol leads to the expected product with a yield of 78% in the form of an almost colourless oil. Scale: 5 mmol.

(b) n-Butyl 6,8-dimercaptooctanoate

According to the same procedure as that described in Example 1(a) for the synthesis of methyl 6,8-dimercaptooctanoate, the reduction of n-butyl lipoate with sodium borohydride gives the expected product with a yield of 95% in the form of an almost colourless oil. Scale: 2 mmol.

(c) n-Butyl 6-S,8-S-bis(3-methylthiopropanoyl)octanoate

According to the same procedure as that described in Example 2 for the synthesis of methyl 6-S,8-S-bis(3-methylthiopropanoyl)octanoate, the acylation of n-butyl 6,8-dimercaptooctanoate with 3 molar equivalents of 3-methylthiopropanoic acid gives the expected product with a yield of 86% in the form of an almost colourless oil. Scale: 4 mmol.

Example 5
Preparation of tert-butyl 6-mercapto-8-S-(3-methylthiopropanoyl)octanoate (compound No.4)

(a) t-Butyl lipoate

The procedure is identical to that described in Example 3(a) for the synthesis of isopropyl lipoate. By esterification of lipoic acid with tert-butanol, the expected product is obtained with a yield of 40% in the form of an almost colourless oil. Scale: 11 mmol.

(b) t-Butyl 6,8-dimercaptooctanoate

According to the same procedure as that described in Example 1(a) for the synthesis of methyl 6,8-dimercaptooctanoate, the reduction of tert-butyl lipoate with sodium borohydride gives the expected product with a yield of 95% in the form of an almost colourless oil. Scale: 11 mmol.

(c) t-Butyl 6-mercapto-8-S-(3-methylthiopropanoyl)octanoate

The procedure is identical to that described in Example 1(a) for the synthesis of methyl 6-mercapto-8-S-(3-methylthiopropanoyl)octanoate. By acylation of t-butyl 6,8-dimercaptooctanoate with the aid of one molar equivalent of 3-methylthiopropanoic acid, the expected product is obtained with a yield of 60% in the form of an almost colourless oil (contaminant: 5% to 10% of t-butyl 6-S-(3-methylthiopropanoyl) 8-mercaptooctanoate). Scale: 10 mmol.

Example 6
Preparation of t-butyl 6-S,8-S-bis(3-methylthiopropanoyl)octanoate (compound No.6)

This compound is prepared according to the same procedure as that described in Example 2 for the synthesis of methyl 6-S,8-S-bis(3-methylthiopropanoyl)octanoate. The acylation of tert-butyl 6,8-dimercaptooctanoate with 3 molar equivalents of 3-methylthiopropanoic acid gives the expected product with a yield of 77% in the form of an almost colourless oil. Scale: 1 mmol.

Example 7
Preparation of (2'-trimethylammoniumethyl) 6-S,8-S-bis(3-methylthiopropanoyl)octanoate iodide (compound No.21)

(a) 2-Dimethylaminoethyl lipoate 12 ml of anhydrous ether are added to 1 g (4.85 mmol) of lipoic acid, 1.1 g (5.33 mmol) of dicyclohexylcarbodiimide and 0.061 g (0.5 mmol) of 4-dimethylaminopyridine placed under nitrogen. After stirring for 10 minutes at room temperature, 0.506 ml (5.33 mmol) of 2-dimethylaminoethanol is added in a single portion and the mixture is stirred for 18 hours. After filtration of the solids and dilution of the filtrate in dichloromethane, it is washed with a saturated aqueous sodium chloride solution. After drying over sodium sulphate and evaporation of the solvent, the crude product is purified by chromatography on silica gel (80 g, eluent: CH$_2$Cl$_2$:MeOH=90/10). 832 mg (62%) of the expected ester are thus isolated in the form of a yellow oil.

(b) 2-Dimethylaminoethyl 6,8-dimercaptooctanoate 134 mg (3.6 mmol) of sodium borohydride are added in two portions, at 0° C., to 820 mg (3.0 mmol) of 2-dimethylaminoethyl lipoate obtained above in solution in 45 ml of a 5/1 methanol/tetrahydrofuran mixture. After stirring for 3 hours at 0° C., 1 N HCl is added dropwise to pH 5 and then the solvent is evaporated off and the residue is taken up in dichloromethane. The solution is washed with a saturated aqueous sodium bicarbonate solution and then with a saturated aqueous sodium chloride solution. After drying over sodium sulphate and evaporation, 780 mg (93%) of the expected dithiol are obtained in the form of an almost colourless oil.

(c) 2-Dimethylaminoethyl 6-S,8-S-bis(3-methylthiopropanoyl)octanoate 1.2 ml of pyridine are added to 233 mg (0.84 mmol) of 2-dimethylaminoethyl 6,8-dimercaptooctanoate in solution in 1.5 ml of dichloromethane and then a solution of 348 mg (2.5 mmol) of 3-methylthiopropanoyl chloride in 2.7 ml of dichloromethane is introduced at 0° C. The mixture is brought to room temperature and stirred for 18 hours. The reaction medium is partitioned between a saturated aqueous sodium bicarbonate solution and dichloromethane. The aqueous phase is then extracted three times with dichloromethane and the organic phase is dried over sodium sulphate. After evaporation, the crude product is purified by chromatography on silica gel (40 g, eluent: $CH_2Cl_2$:MeOH=96/4). 242 mg (60%) of the expected product are thus isolated in the form of an oil.

(d) (2'-Trimethylammoniumethyl) 6-S,8-S-bis(3-methylthiopropanoyl) octanoate iodide 0.048 ml (0.77 mmol) of methyl iodide is added to 250 mg (0.52 mmol) of 2-dimethylaminoethyl 6-S,8-S-bis(3-methylthiopropanoyl)octanoate in 5.2 ml of ethyl acetate, at room temperature and then the stirring is continued for 5 hours. The solvent is then evaporated off under vacuum and the residue is taken up in 5 ml of anhydrous ether and the ether phase is removed. The crude product is purified by chromatography on silica gel (5 g, eluent: $CH_2Cl_2$:MeOH=90/100). 264 mg (81%) of the expected ammonium salt are isolated in a noncrystallized and hygroscopic form.

Example 8

Preparation of [6-S,8-S-bis(3-methylthiopropanoyl) octanoyl]-N-ethylpiperazine (compound No.22)

(a) (Lipoyl)-N-methylpiperazine

A solution of 107 mg (1.07 mmol) of N-methylpiperazine in 1.2 ml of dichloromethane is added at room temperature to 200 mg (0.97 mnol) of lipoic acid, 240 mg (1.16 mmol) of dicyclohexylcarbodiimide and 12 mg (0.1 mmol) of 4-dimethylaminopyridine in 1 ml of dichloromethane. After stirring for 23 hours, filtration of the solids and dilution of the filtrate in dichloromethane, the mixture is washed with a saturated aqueous sodium chloride solution. After drying over sodium sulphate and evaporation of the solvent, the crude product is purified by chromatography on silica gel (22 g, eluent: $CH_2Cl_2$:MeOH=92/8). 216 mg (77%) of the expected amide are isolated in the form of a yellow oil.

(b) (6,8-Dimercaptooctanoyl)-N-methylpiperazine)

This compound is obtained according to the same procedure as that described in Example 7(b) by reduction of (lipoyl)-N-methylpiperazine with sodium borohydride. The expected product is obtained with a yield of 94% in the form of an almost colourless oil. Scale: 0.4 mmol.

(c) [6-S,8-S-Bis(3-methylthioropanoyl)octanoy]-N-methylpiperazine

The procedure is identical to that described in Example 7(c) for the synthesis of 2-dimethylaminoethyl 6-S,8-S-bis (3-methylthiopropanoyl)octanoate. The acylation of (6,8-dimercaptooctanoyl)-N-methylpiperazine with 3 molar equivalents of 3-methylthiopropanoyl chloride gives the expected product with a yield of 90% in the form of an almost colourless oil. Scale: 0.4 mmol.

Example 9

Preparation of methyl 6-S-(3-methylthiopropanoyl) 8-S-acetyl octanoate (compound No.24)

(a) methyl 6-mercapto 8-S-acetyl octanoate

To a mixture of 3.045 g (13.7 mmol) of methyl 6,8-dimercapto octanoate as obtained in Example 1(a) and 11.08 ml (13.7 mmol) of pyridine, 1.29 ml (13.7 mmol) of acetic anhydride are dropwise added at 0° C. The temperature is then raised to ambient with stirring for 20 hours.

After ether dilution, the organic phase is washed with hydrochloric acid (1N) and with a saturated sodium chloride solution. After drying on sodium sulfate, the solvent is evaporated and the crude product is purified by chromatography on silica gel (200 g: eluent petroleum ether/ethyl acetate 90/10). The expected product is obtained with a yield of 61% (2.235 g) in the form of a slightly yellow oil (contaminant: about 10% of methyl 6-S-acetyl 8-mercapto octanoate).

(b) 6-S-(3-methylthiopropanoyl) 8-S-acetyl octanoate 1.76 ml (10.1 mmol) of diisopropylethylamine are added to a solution of 2.23 g (8.4 mmol) of methyl 6-mercapto 8-S-acetyl octanoate in 35 ml of dichloromethane. Then a solution of 1.403 g (10.1 mmol) of 3-methylthiopropanoyl chloride in 5 ml of dichloromethane is added at –50° C. and the temperature of the reaction mixture is raised to –25° C. within 30 mn.

After ether dilution, the organic phase is washed with a saturated sodium chloride solution. After drying on sodium sulfate, the solvent is evaporated and the crude product is purified by chromatography on silica gel (200 g: eluent petroleum ether/ethyl acetate 90/10). 2.96 g (96%) of the expected product are obtained (contaminant: about 10% of methyl 6-S-acetyl 8-S-(3-methylthiopropanoyl)octanoate).

Example 10

Preparation of methyl 6-S-acetyl 8-S-(3-methylthiopropanoyl)octanoate (compound No.23)

(a) 3-methylthiopropanoic acid anhydride 378 mg (1.83 mmol) of dicyclohexylcarbodiimide are added to a solution of 0.345 ml (3.33 mmol) of 3-methylthiopropanoic acid in 9 ml of ether. After 24 hours at ambiant temperature, the mixture is filtered to eliminate the resulting dicyclohexylurea and the filtrate is evaporated to dryness. The expected anhydride is obtained in quantitative yield and is directly used for the next step.

(b) methyl 6-mercapto, 8-S-(3-methylthiopropanoyl) octanoate

This compound is obtained according to the same procedure as that described in Example 9(a) for the synthesis of methyl 6-mercapto 8-S-acetyl octanoate by replacing acetic anhydride with 3-methylthiopropanoic acid anhydride as described in (a) above. The expected product is obtained with a yield of 60% (contaminant: about 10% of methyl 6-S-(3-methylthiopropanoyl) 8-mercapto octanoate).

Scale: 1.7 mmol

The product was purified by chromatography on silica gel (60 g: eluent petroleum ether/ethyl acetate 90/10).

(c) methyl 6-S-acetyl 8-S-(3-methylthiopropanoyl) octanoate

According to the same procedure as that described in Example 9(a) for the synthesis of methyl 6-mercapto 8-S-acetyl octanoate (acylation with acetic anhydride in pyridine). The expected product is obtained with a yield of 88% (contaminant: about 10% of methyl 6-S-(3-methylthiopropanoyl) 8-S-acetyl octanoate).

Scale: 0.4 mmol

The product was purified by chromatography on silica gel (5 g: eluent petroleum ether/ethyl acetate 85/15).

STUDIES OF ACTIVITY

I- Effect of the Compounds Nos. 1(RS), 1(S), 1(R), 3(RS), 4(RS), 6(RS), 9(RS), 21(RS) and 24(RS) on the Growth of Tumor Cell Lines and Nonneoplastic Cell Lines The growth-inhibiting activity of the compounds of the invention was tested either on HeLa cells obtained from a cancer of the uterus, either on prostate cancer cell lines from human, ie., DU 145, PC3 and LNCaP, or on B16 murine melanoma cells, and on human pulmonary fibroblasts MRC-5 of embryonic origin.

The cell lines were plated on a Petri dish at a concentration of $0.5 \times 10^6$ and are cultured in 3 ml of Eagle's essential medium containing 10% by volume of dialyzed foetal calf serum.

After 4 hours, the cells are cultured in presence of the various test compounds at increasing concentrations (1 to 800 μM). After incubation for 72 hours, the cells are washed twice in a phosphate-buffered saline medium pH 7.5 (PBS buffer) and then recovered in the same PBS buffer.

The inhibition of cell growth is evaluated either by measuring the content of proteins according to the method described by Lowry et al. (J. Biol. Chem., 193, 265, 1951), or by measuring the DNA content with the aid of the Hoechst dye according to the method described by West et al. (Analytical Biochem. 147, 289 (1985), or alternatively by determining the activity of dehydrogenases according to the method described by Mosmann T. (J. Immunol. Methods, 65, 55, 1983).

Results of selective inhibition of cell growth for compounds Nos. 1 (RS), 1(R), 1(S), 3(RS), 4(RS), 6(RS), 9(RS), 21 (RS) and 24(RS) are assembled in FIGS. 3 to 11.

Figure 3:
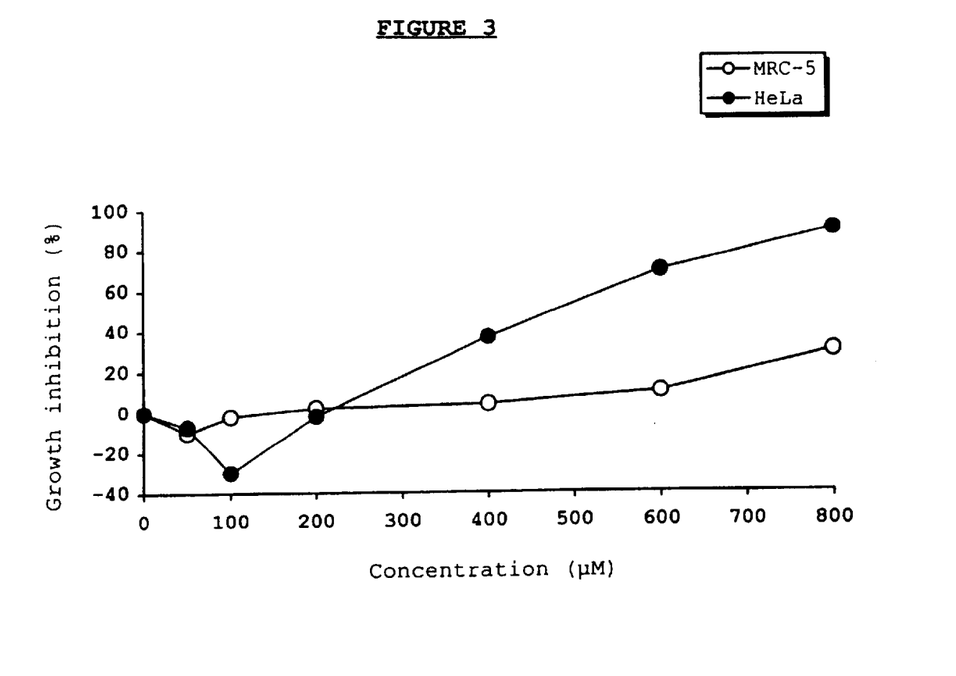
FIG. 3 is a graph demonstrating the inhibition of growth of HeLa cells (—●—) and MRC-5 cells (—○—) after incubation with increasing concentrations of compound No.1(RS).

The results as presented in FIG. 3 clearly show that the compound No.1(RS) is capable of inducing inhibition of growth of HeLa cells by 40% at a concentration of 400 μM and by 70% at a concentration of 600 μM whereas the inhibition of growth of fibroblastic cells MRC-5 does not exceed 5–10% at the same concentrations.

Figure 4:
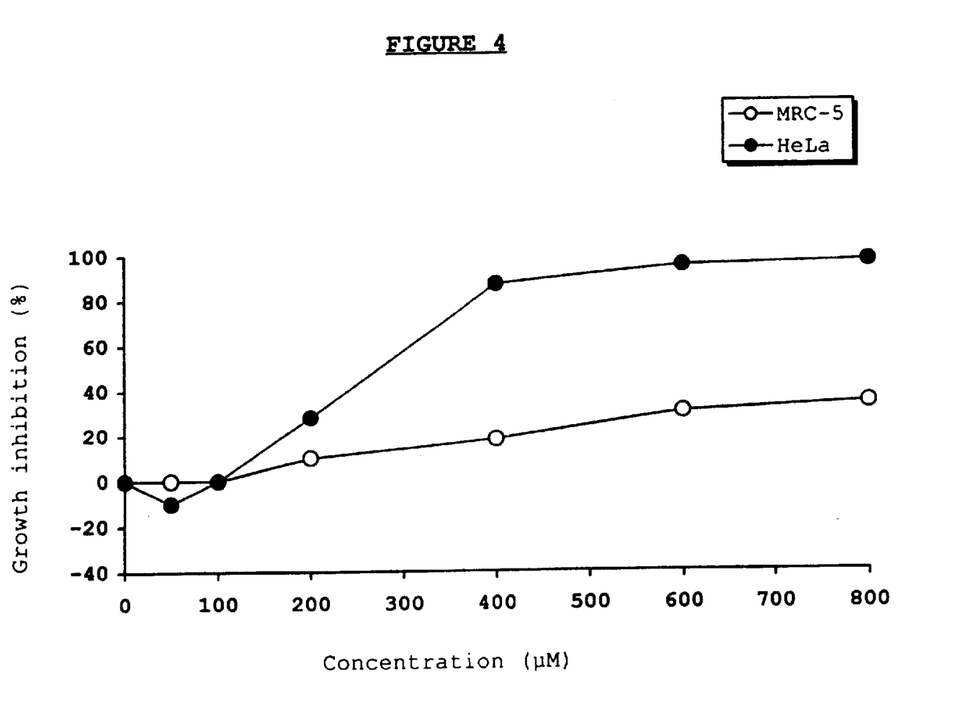
FIG. 4 is a graph demonstrating the inhibition of growth of HeLa cells (—●—) and MRC-5 cells (—○—) after incubation with increasing concentrations of compound No.1(S).

Compound No.1(S) also selectively inhibits the growth of HeLa cells, by 90% at a concentration of 400 μM and by 100% at a concentration of 600 μM, whereas the inhibition of growth of MRC-5 cells does not exceed 20% even at higher concentrations of between 600 and 800 μM (see FIG. 4).

Figure 5:
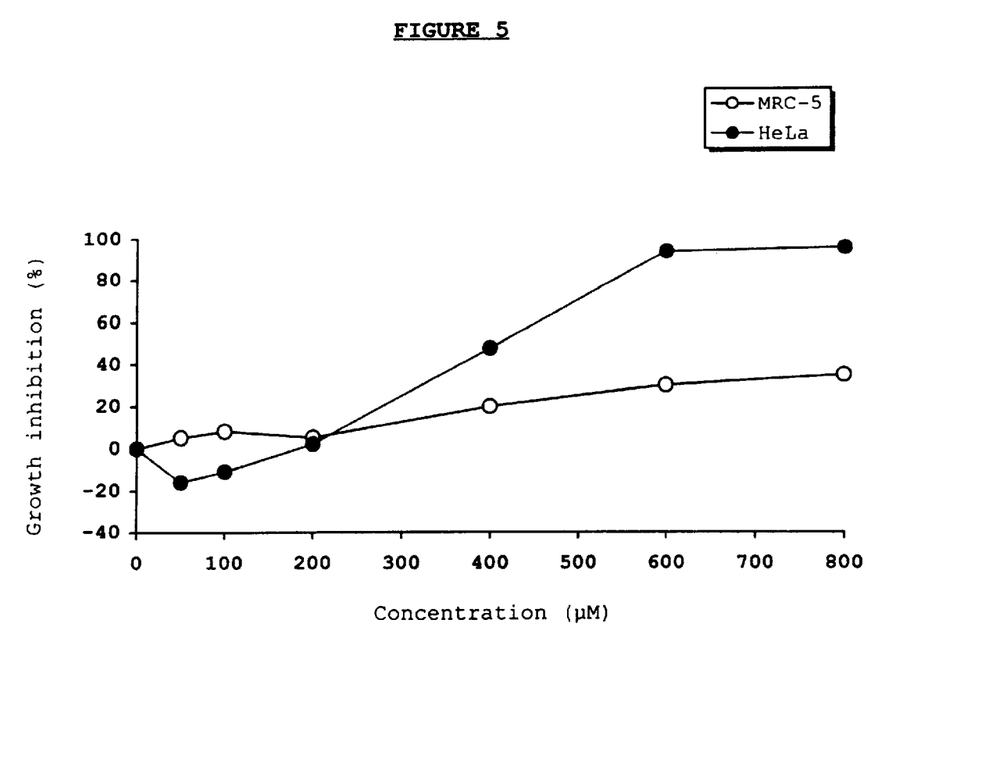
FIG. 5 is a graph demonstrating the inhibition of growth of HeLa cells (—●—) and MRC-5 cells (—○—) after incubation with increasing concentrations of compound No.1(R).

Further, compound No.1(R) inhibits the growth of HeLa cells by 40% at a concentration of 400 μM, and by 100% at concentrations of between 600 and 800 μM (see FIG. 5).

Compound No.1, either in its racemic form, or in the form of one of its enantiomers, is capable of inhibiting, at concentrations of between 400 and 600 μM, selectively and effectively, the growth of HeLa cells while inhibiting only slightly that of nonneoplastic fibroblastic cells MRC-5.

Figure 6:
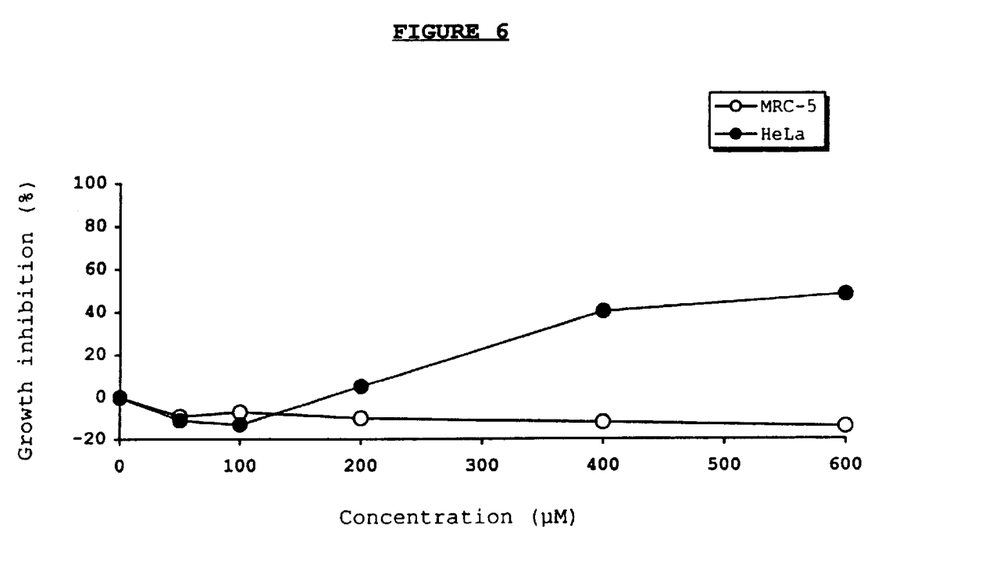
FIG. 6 is a graph demonstrating the inhibition of growth of HeLa cells (—●—) and MRC-5 cells (—○—) after incubation with the racemate of increasing concentrations of compound No.3(RS).

Moreover, the results obtained with compound No.3(RS) as displayed in FIG. 6, show that at concentrations of between 200 and 600 μM, compound No.3(RS) induces a 50% inhibition of growth of HeLa cells whereas growth of MRC-5 cells is not changed.

Figure 7:
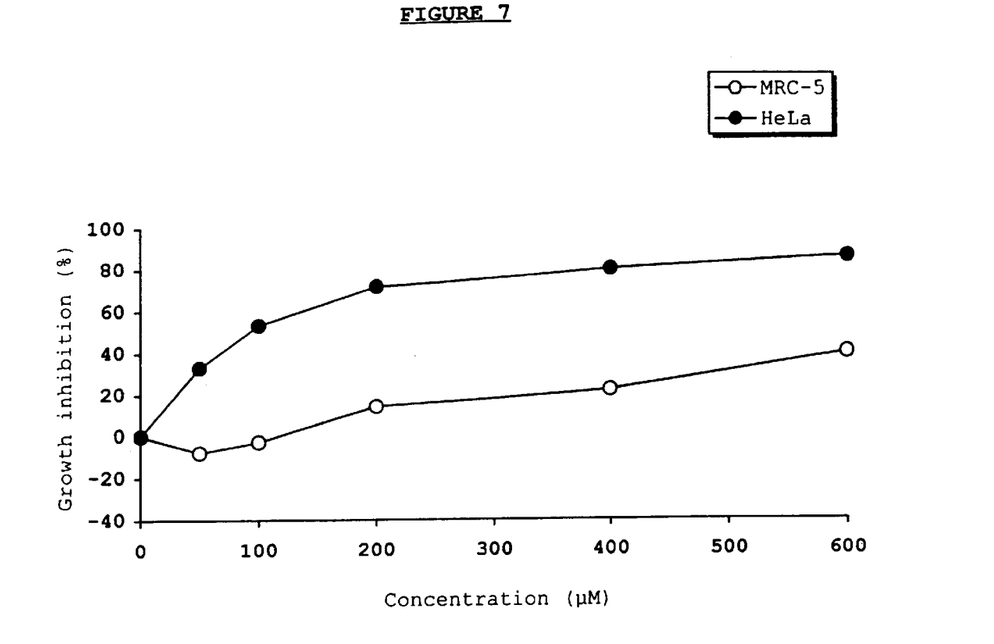
FIG. 7 is a graph demonstrating the inhibition of growth of HeLa cells (—●—) and MRC-5 cells (—○—) after incubation with increasing concentrations of compound No.4(RS).
Figure 8:
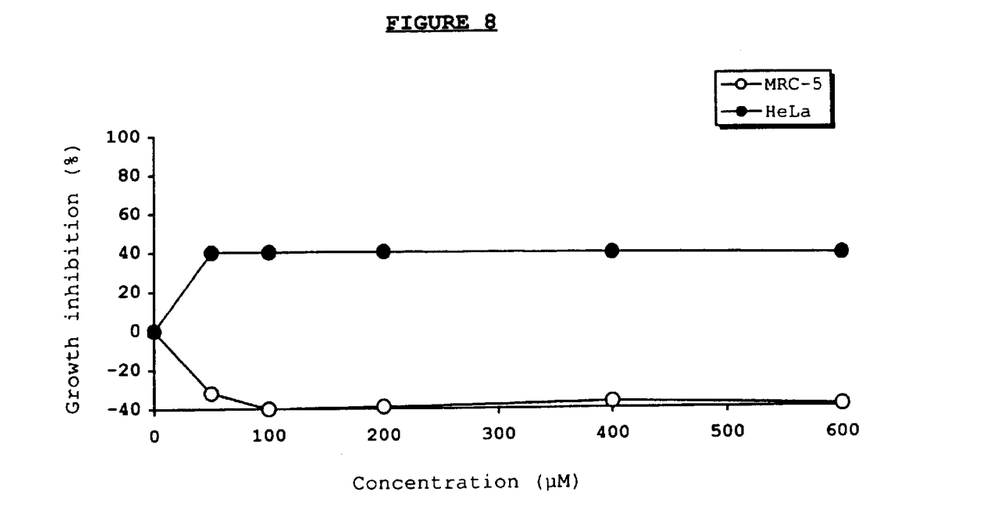
FIG. 8 is a graph demonstrating the inhibition of growth of HeLa cells (—●—) and MRC-5 cells (—○—) after incubation with increasing concentrations of compound No.6(RS).
Figure 9:
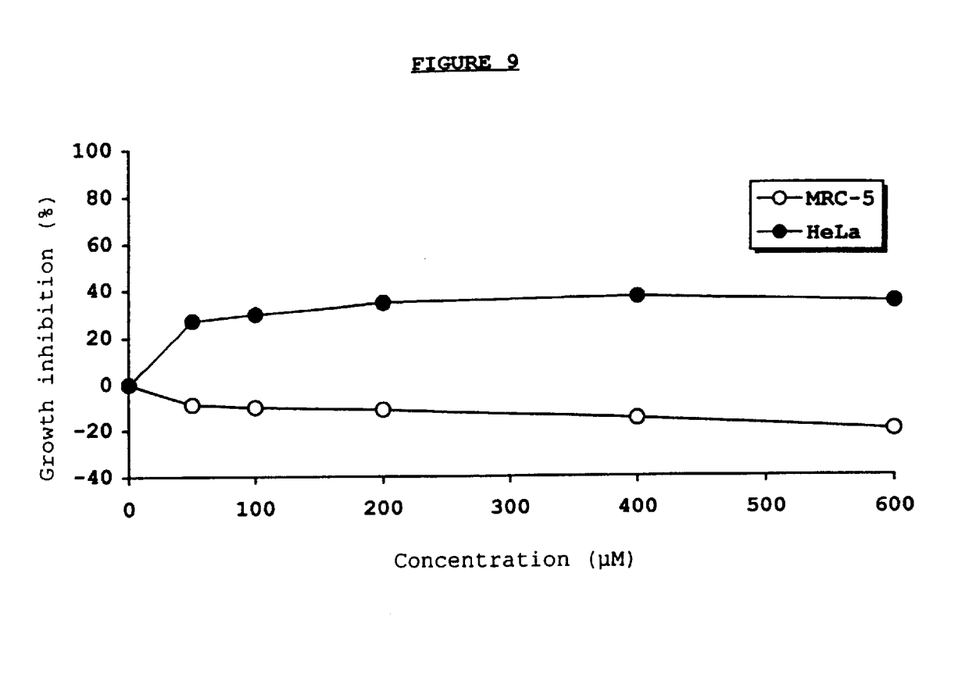
FIG. 9 is a graph demonstrating the inhibition of growth of HeLa cells (—●—) and MRC-5 cells (—○—) after incubation with increasing concentrations of compound No.9(RS).

According to the results illustrated in FIG. 7, compound No.4(RS) is a highly selective inhibitor of growth of HeLa cells, since it induces a 70% inhibition of growth of HeLa cells at 200 μM, whereas the growth of MRC-5 cells is only inhibited by 20% at an equivalent concentration.

Compound No.6 in its racemic form is capable of inhibiting at concentrations of between 50 and 600 μM selectively and effectively the growth of HeLa cells. On the other hand, the growth of MRC-5 cells is stimulated by about 40% (See FIG. 8).

Compound No.9 in its racemic form is capable of inhibiting at concentrations of between 50 and 600 μM selectively and effectively the growth of HeLa cells. On the other hand, the growth of MRC-5 cells is stimulated by about 20% (See FIG. 9).

Figure 10:
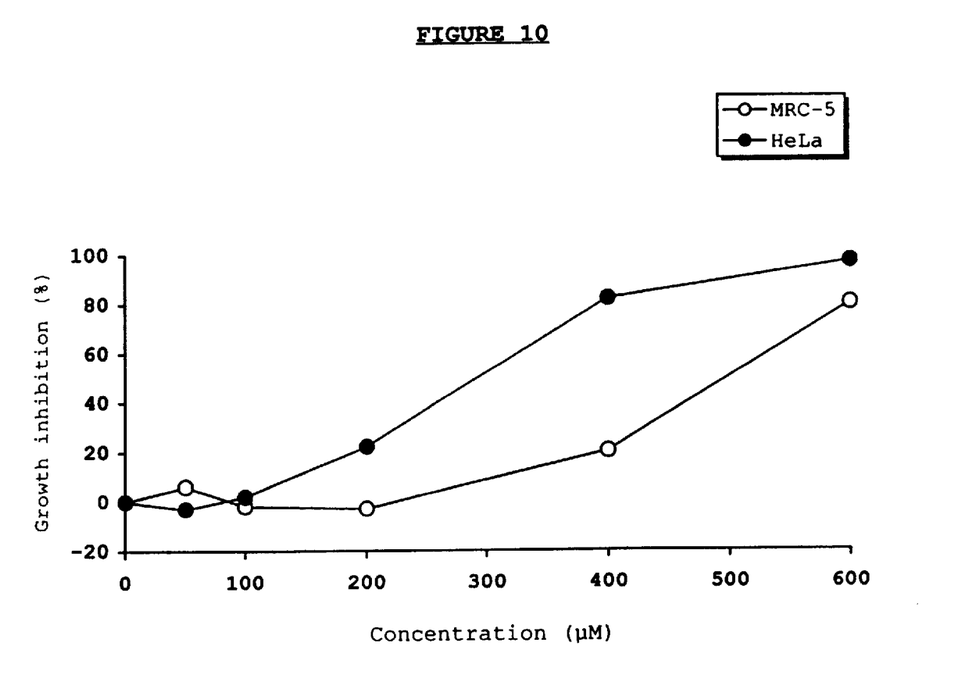
FIG. 10 is a graph demonstrating the inhibition of growth of HeLa cells (—●—) and MRC-5 cells (—○—) after incubation with increasing concentrations of compound No.21(RS).
Figure 11:
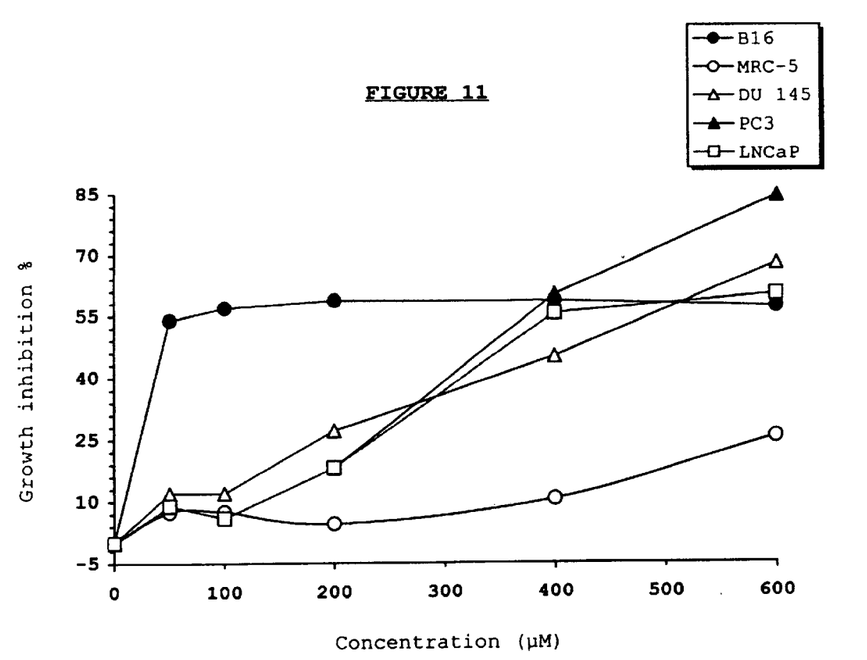
FIG. 11 is a graph demonstrating the inhibition of growth of B16 cells (—●—) DU 145 cells (—△—), PC3 cells (—▲—), LNCaP cells (—□—) and MRC-5 cells (—○—) after incubation with increasing concentrations of compound No.24(RS).

The results presented in FIG. 10 show that compound No.21 in its racemic form is capable of inhibiting the growth of transformed HeLa cells by 80% at 400 μM whereas that of MRC-5 cells is inhibited by only 20%.

Similar results were observed in relation to the R and S stereoiosomers of compounds 6, 9 and 21.

Finally, racemic form of compound 24 was tested on the prostate cancer cell lines, DU 145, PC3, LNCaP and on B16 murine melanoma cells, showing a 50–60% growth inhibition at a concentration of 400 μM. When tested at the same concentration on MRC-5 cells, compound 24 induces a 10% growth inhibition only (see FIG. 11).

This inhibition of growth of tumour cell lines, such as HeLa cells, is due to the increase in the percentage of cells entering apoptosis, as demonstrated below. Indeed, the percentage of DNA fragmentation is correlated with the phenomenon of apoptosis.

II: Effect of compound No.1 (RS) as agent inducing apoptosis measured by DNA fragmentation quantitative assay in HeLa cells Quantitative analysis of the DNA fragments smaller than 3 Kb in size was carried out according to the method described by Wright S. et al. (J. Cell. Biochem., 48, 344–355), by incubating $2.5 \times 10^5$ HeLa cells/ml with 0.5 μCi [$^3$H]thymidine for 40 hours at 37° C. After two washes with the culture medium, the cells are cultured in presence of compound No.1 (RS), 200 μM. After incubating for 6 hours, the cells are recovered by centrifugation at 400 g for 5 minutes and washed three times in PBS buffer. The cells recovered in the pellet are lysed in 2 ml containing 0.1% Triton X-100, 20 mM EDTA, 5 mM Tris pH 8 and centrifuged at 30,000 g at 4° C. for 30 minutes. The supernatants are recovered and the pellets dissolved in 0.3 ml of 0.5 N NaOH. Aliquots of the culture medium (1 ml), of the supernatant (0.3 ml) and of the solubilized pellet (0.1 ml) are assayed in a scintillation counter.

The percentage of DNA fragments is calculated in the following manner:

$$\% \text{ of fragments} = \frac{\text{dpm of culture medium} + \text{dpm of DNA supernatant}}{\text{dpm of culture medium} + \text{dpm of supernatant} + \text{dpm of solubilzed pellet}}$$

Figure 12:
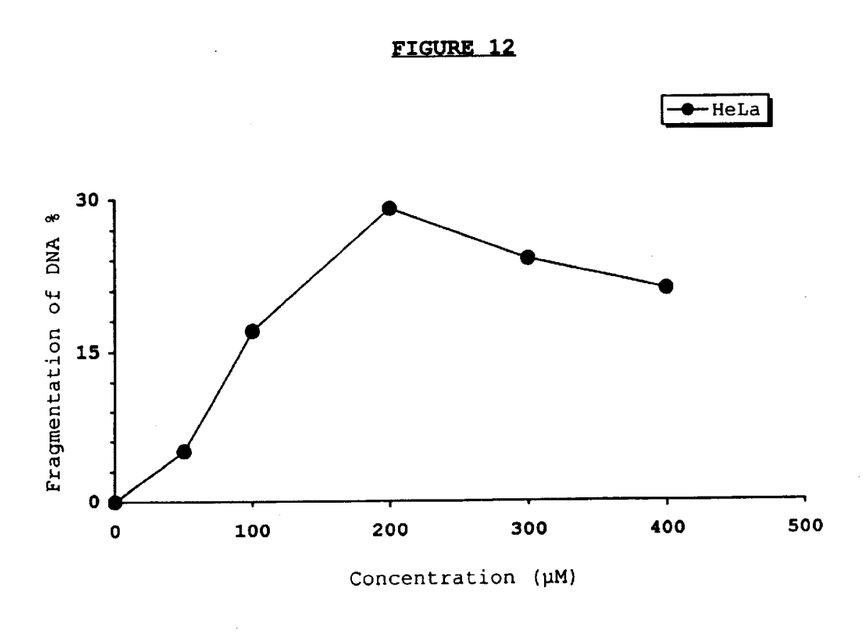
FIG. 12 illustrates quantification of DNA fragmentation in HeLa cells after incubation with 200 μM of compound No.1(RS) by radiolabelling.

The results which are assembled in FIG. 12 clearly show that compound No.1 (RS) induces an increase of DNA fragmentation in the HeLa cells of approximately 17% at 100 μM and 30% at 200 μM.

III: In vivo antitumour effect of Compound No.1(RS)

Antitumour effect of compound No.1(RS) was tested in vivo on B6D2F1 mice (IFFA CREDO, France) which received at t=0 day, $2 \times 10^5$ B16 murine melanoma cells by subcutaneous injection.

At t=1 day, and continuously for 15 days, the mice were injected intraperitoneally with the following solutions: 10% ethanol in a 0.14 M aqueous NaCl solution, and compound No.1 (RS) either at 50 mg/kg or at 100 mg/kg.

The growth of the tumour was then observed over a period ranging from 10 to 60 days. The results are expressed as a percentage of mice bearing tumours.

Figure 13:
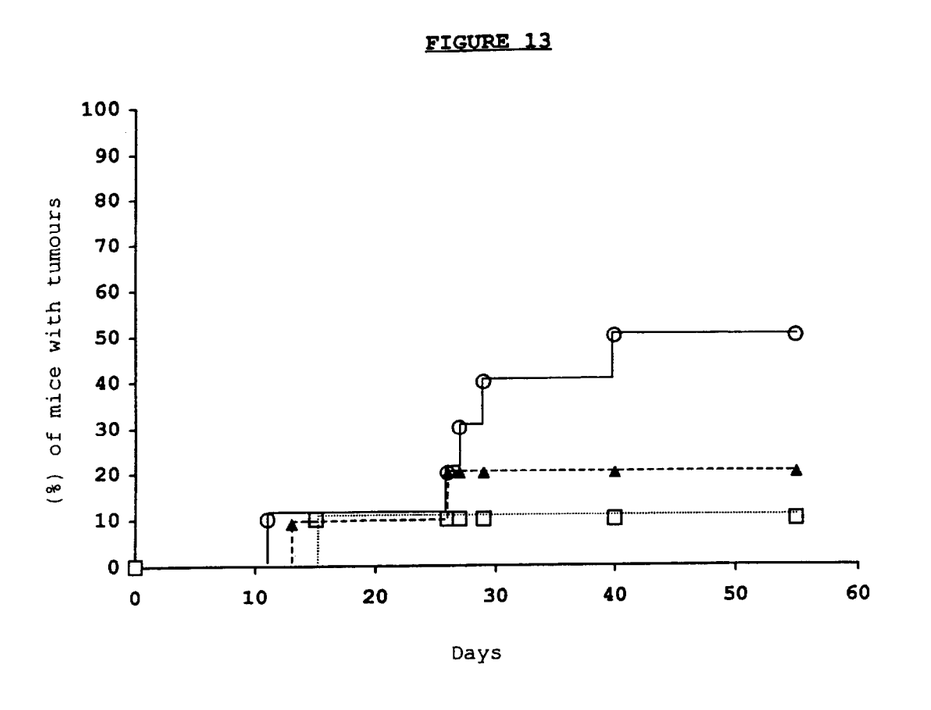
FIG. 13 represents tumour growth in mice which are injected for 15 days with 10% ethanol in 0.14 M NaCl (—○—); and compound No.1(RS) at 50 mg/kg (—▲—), at 100 mg/kg (—□—).

FIG. 13 shows that compound No.1 (RS) is very effective for controlling the growth of the tumour. In effect, the percentage of mice having tumours reaches 50% in the controls which have received the vehicle consisting of 10% ethanol in a 0.14 M aqueous NaCl solution, whereas it reaches 20% and 10% in mice having received compound No.1(RS) at 50 mg/kg and 100 mg/kg, respectively.

We claim:
1. 6,8-Dimercaptooctanoic acid derivatives substituted at the 6-S and/or 8-S position with the (3-methylthiopropanoyl) radical having the following formula (I):

in which:
R represents $OR_3$ or

$R_3$ representing a hydrogen atom, a linear or branched alkyl radical, or a radical of the formula n being an integer from 1 to 10 and r' and r", which are identical or different, representing a hydrogen atom, a linear or branched alkyl radical, or taken together, form with the nitrogen atom, a nitrogen-containing heterocycle optionally substituted with an optionally substituted oxygen or nitrogen atom, $R_5$ and $R_4$, identical or different, represent a hydrogen atom, or a linear or branched alkyl radical, and $R_1$ and $R_2$, which are identical or different, represent a hydrogen atom, a radical —$COCH_3$ or a radical of formula:

(II)

with the proviso that at least one of the radicals $R_1$ or $R_2$ represents a radical of formula (II) and the R and S enantiomers and their racemate as well as the salts of the said compounds of formula (I).

2. Compounds according to claim 1, wherein the linear or branched alkyl radical represented by r', r", $R_4$ or $R_5$ contains 1 to 6 carbon atoms.

3. Compounds according to claim 1, wherein the index "n" is comprised between 2 and 6, the divalent radical being preferably selected from ethylene, propylene, butylene or methyl-2 propane-1,2 diyl.

4. Compounds according to claim 1, wherein the nitrogen-containing heterocycle is selected from morpholine, pyrrolidine, piperazine, homopiperazine and a N-alkyl ($C_1$–$C_6$) piperazine.

5. Compounds according to claim 1, wherein the salts are selected from the salts with a mineral or organic base when said compounds contain a carboxylic acid function.

6. Compounds according to claim 1, wherein the salts are selected from the salts with a mineral or organic acid when said compounds contain a salifying amino function.

7. Compounds according to claim 6, wherein the salts are selected from halides, nitrates, sulfates, sulfonates, carboxylates, thiocyanates and phosphates.

8. Compounds according to claim 1 selected from the group consisting of:

methyl 6-mercapto-8-S-(3-methylthiopropanoyl) octanoate,
methyl 6-S-(3-methylthiopropanoyl) 8-mercaptooctanoate,
methyl 6-S,8-S-bis(3-methylthiopropanoyl)octanoate,
tert-butyl 6-mercapto-8-S-(3-methylthiopropanoyl) octanoate,
tert-butyl 6-S-(3-methylthiopropanoyl) 8-mercaptooctanoate,
tert-butyl 6-S,8-S-bis(3-methylthiopropanoyl)octanoate,
n-butyl 6-mercapto-8-S-(3-methylthiopropanoyl) octanoate,
n-butyl 6-S-(3-methylthiopropanoyl) 8-mercaptooctanoate,
n-butyl 6-S,8-S-bis(3-methylthiopropanoyl)octanoate,
6-mercapto-8-S-(3-methylthiopropanoyl)octanoic acid,
6-S-(3-methylthiopropanoyl) 8-mercaptooctanoic acid,
6-S,8-S-bis(3-methylthiopropanoyl)octanoic acid,
ethyl 6-mercapto-8-S-(3-methylthiopropanoyl)octanoate,
ethyl 6-S-(3-methylthiopropanoyl) 8-mercaptooctanoate,
ethyl 6-S,8-S-bis(3-methylthiopropanoyl)octanoate,
isopropyl 6-mercapto-8-S-(3-methylthiopropanoyl) octanoate,
isopropyl 6-S-(3-methylthiopropanoyl) 8-mercaptooctanoate,
isopropyl 6-S,8-S-bis(3-methylthiopropanoyl)octanoate,
(2'-trimethylammoniumethyl) 6-mercapto-8-S-(3-methylthiopropanoyl) octanoate iodide,
(2'-trimethylammoniumethyl) 6-S-(3-methylthiopropanoyl) 8-mercaptooctanoate iodide,
(2'-trimethylammoniumethyl) 6-S,8-S-bis(3-methylthiopropanoyl)octanoate iodide,
[6-S,8-S-bis(3-methylthiopropanoyl)octanoyl]N-methylpiperazine,
methyl 6-S-acetyl, 8-S-(3-methylthiopropanoyl) octanoate,
methyl 6-S-(3-methylthiopropanoyl), 8-S-acetyl octanoate,
(2'-trimethylammoniumethyl) 6-S-acetyl, 8-S-(3-methylthiopropanoyl) octanoate iodide, and
(2'-trimethylammoniumethyl) 6-S-(3-methylthiopropanoyl), 8-S-acetyl octanoate iodide.

9. Pharmaceutical composition comprising an effective amount of at least one active compound according to claim 1 in a pharmaceutically acceptable excipient.

10. Pharmaceutical composition according to claim 9, comprising an effective amount of said active compound to induce apoptosis of cancer cells in a human or animal subject.

11. Pharmaceutical composition according to claim 9, comprising an effective amount of said active compound for the treatment, regression and prevention of cancer in a human or animal subject.

12. Pharmaceutical composition according to any of claim 10 or 11, wherein the effective amount is between 0.1 and 10% by weight relative to the total weight of the composition.

13. Pharmaceutical composition according to any of claim 10 or 11, wherein the effective amount is between 0.1 and 5% by weight relative to the total weight of the composition.

14. A method of inducing apoptosis of cancer cells in a human or an animal subject which comprises administering to the subject an effective amount of said active compound of claim 1.

15. A method for treatment, regression, and prevention of cancer in a human or an animal which comprises administering to the subject an effective amount of said active compound of claim 1.

16. The method of any of claim 14 or 15 or wherein the administration is parenteral, enteral, or topical.

17. The method of claim 16, wherein a daily dose of 50 mg/kg to 100 mg/kg of bodyweight is administered.

* * * * *

UNITED STATES PATENT AND TRADEMARK OFFICE
CERTIFICATE OF CORRECTION

PATENT NO.     : 6,117,902
DATED          : September 12, 2000
INVENTOR(S)    : Quash et al.

Page 1 of 1

It is certified that error appears in the above-identified patent and that said Letters Patent is hereby corrected as shown below:

<u>Column 2,</u>
Line 45, "firther" should read -- further --

<u>Column 7,</u>
Line 29, "containing," should read -- containing --

<u>Column 11,</u>
Line 31, "ethylpiperazine" should read -- methylpiperazine --
Line 51, "methylthioropanoyl)octanoy]" should read
-- methylthiopropanoyl)octanoyl] --

<u>Column 12,</u>
Line 19, "mn." should read -- min. --
Line 34, "ambiant" should read -- ambient --

<u>Column 13,</u>
Line 2, "ie.," should read -- i.e., --
Line 20, "Kb" should read -- kb --

<u>Column 18,</u>
Line 1, delete "any of"

Signed and Sealed this

Fifth Day of March, 2002

*Attest:*

*Attesting Officer*

JAMES E. ROGAN
*Director of the United States Patent and Trademark Office*